United States Patent [19]

Ditgens et al.

[11] Patent Number: 4,717,415
[45] Date of Patent: Jan. 5, 1988

[54] HERBICIDAL COMPOSITIONS OF TRIAZINONE OR TRIAZINEDIONE DERIVATIVES AND HALOALKANOIC ACID AMIDE SYNERGISTS

[75] Inventors: Klaus Ditgens; Ulrich Heinemann; Winfried Lunkenheimer; Hans-Jochem Riebel; Jörg Stetter; Rudolf Thomas, all of Wuppertal; Carl Fedtke, Cologne, all of Fed. Rep. of Germany

[73] Assignee: Bayer Aktiengesellschaft, Leverkusen, Fed. Rep. of Germany

[21] Appl. No.: 796,386

[22] Filed: Nov. 8, 1985

Related U.S. Application Data

[63] Continuation of Ser. No. 534,536, Sep. 22, 1983, abandoned.

[30] Foreign Application Priority Data

Oct. 13, 1982 [DE] Fed. Rep. of Germany ........ 3238007

[51] Int. Cl.[4] ............................................. A01N 43/64
[52] U.S. Cl. ......................................... 71/93; 71/88; 71/92; 71/94; 71/118
[58] Field of Search ............................. 71/88, 93, 118

[56] References Cited

U.S. PATENT DOCUMENTS

| | | | |
|---|---|---|---|
| 3,847,914 | 11/1974 | Dickore et al. | 71/93 |
| 4,021,224 | 5/1977 | Pallos et al. | 71/118 |
| 4,056,527 | 11/1977 | Schlee et al. | 71/93 |
| 4,124,376 | 11/1978 | Pallos et al. | 71/118 |
| 4,137,070 | 1/1979 | Pallos et al. | 71/118 |
| 4,294,967 | 10/1981 | Riebel et al. | 546/242 |
| 4,392,882 | 7/1983 | Riebel et al. | 71/92 |
| 4,396,416 | 8/1983 | Riebel et al. | 71/92 |
| 4,415,353 | 11/1983 | Pallos et al. | 71/100 |

FOREIGN PATENT DOCUMENTS

| | | |
|---|---|---|
| 1542873 | 7/1970 | Fed. Rep. of Germany . |
| 2828331 | 1/1980 | Fed. Rep. of Germany . |
| 2828265 | 1/1980 | Fed. Rep. of Germany . |

OTHER PUBLICATIONS

East Ger. DD 152, 904, (12-16-81), Chem. Abst., vol. 97, (1982), 34710z.
Annon. Res. Discl., Chem. Abst. vol. 88, (1978), 99991a.
Hansen et al., Chem. Abst., vol. 92, (1980), 210194s.

*Primary Examiner*—Catherine L. Mills
*Attorney, Agent, or Firm*—Sprung, Horn, Kramer & Woods

[57] ABSTRACT

Herbicidal compositions comprising

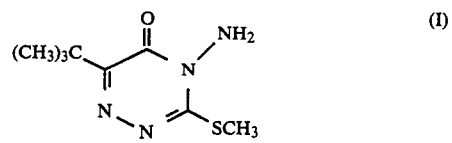

(I)

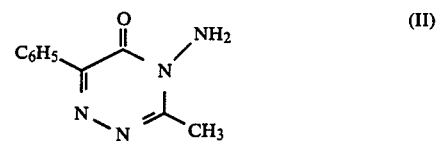

(II)

or

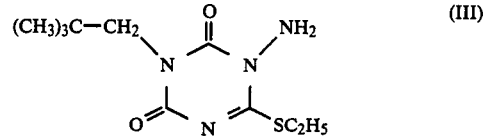

(III)

and as a synergist an amide of the formula

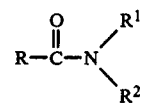

in which
R is halogenoalkyl.

10 Claims, No Drawings

HERBICIDAL COMPOSITIONS OF TRIAZINONE OR TRIAZINEDIONE DERIVATIVES AND HALOALKANOIC ACID AMIDE SYNERGISTS

This is a continuation of application Ser. No. 534,536, filed Sept. 22, 1983 and now abandoned.

The present invention relates to new herbicidal synergistic active compound combinations which consist of known triazinone derivatives or triazonedione derivatives on the one hand and of halogenocarboxylic acid amides, some of which are known, on the other hand.

It has already been disclosed that certain triazinone derivatives or triazinedione derivatives, such as, for example, 4-amino-6-t-butyl-3-methylthio-1,2,4-triazin-5-one or 4-amino-3-methyl-6-phenyl-1,2,4-triazin-5-one or 1-amino-6-ethylthio-3-neopentyl-1,3,5-triazine-2,4-dione, possess herbicidal properties (see DE-OS (German Published Specification ) No. 1,542,873, U.S. Pat. No. 3,847,914, issued Nov. 12, 1974, and U.S. Pat. No. 4,056,527, issued Nov. 1, 1977. However, the disadvantage of these herbicidal substances is that they are not always completely satisfactory in the case of all weeds and graminaceous weeds which occur, or that when appropriately high amounts are used, some species of crop plants are partially damaged.

Furthermore, it is known that the selectivity of herbicidal acetanilides and thiolcarbamates can be improved by the addition of halogenocarboxylic acid amides. Thus, for example, mixtures of N,N-diallyl-dichloroacetamide and herbicidal acetanilides or thiolcarbamates can be used in corn, whereas when the herbicidal acetanilides or thiocarbamates are used without the addition of N,N-diallyl-dichloroacetamide, the corn plants are severely damaged (see, for example, U.S. Pat. specification No. 4,021,224, U.S. Pat. specification No. 4,124,376 and U.S. Pat. specification No. 4,137,070.)

It has now been found that the new active compound combinations consisting of (1) a known herbicidal active compound from the class comprising the triazinones or triazinediones of the formula (I), (II) or (III) (herbicides)

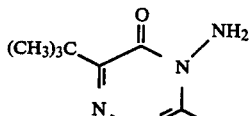

(I)

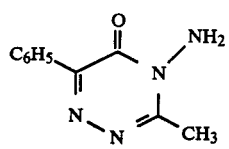

(II)

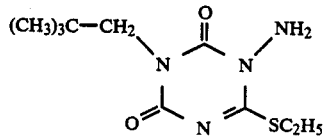

(III)

and (2) a halogenocarboxylic acid amide of the general formula (IV) (synergistic agents)

(IV)

in which

R represents halogenoalkyl and $R^1$ and $R^2$ are identical or different and represent hydrogen, optionally substituted alkyl, optionally substituted alkenyl, alkinyl, optionally substituted cycloalkyl, cycloalkenyl, amino, alkylthio, alkyidenamino, formyl, optionally substituted alkylcarbonyl, optionally substituted alkoxycarbonyl, optionally substituted alkylamino, optionally substituted phenyl or phenylsulphonyl or optionally substituted heteroaryl, or $R^1$ and $R^2$, together with the nitrogen atom to which they are bonded, represent optionally substituted piperidinyl or piperidonyl, perhydroazepinyl, perhydroazocinyl, optionally substituted dihydropyrazolyl, optionally substituted morpholinyl, optionally substituted perhydro-1,3-oxazinyl, optionally substituted 1,4-piperazinyl, optionally substituted perhydro-1,4-diazepinyl, optionally substituted dihydro-, tetrahydro- or perhydroquinolyl or -isoquinolyl, optionally substituted dihydro- or perhydroindolyl, optionally substituted dihydro- or tetrahydropyridyl, azabicyclononyl, optionally substituted pyrrolidinyl or optionally substituted oxazolidinyl, possess particularly high herbicidal activity.

Surprisingly, the herbicidal activity of the active compound combinations according to the invention is substantially higher than the sum of the actions of the individual active compounds. In particular, the halogenocarboxylic acid amides of the general formula (IV), some of which are known, do not themselves possess any herbicidal action when used in the customary amounts, but effect an increase in the herbicidal action of the herbicidal triazinones or triazinediones of the formulae (I), (II) or (III). To this extent, the synergistic effect found in this case is completely unexpected and surprising.

Since the synergistic effect also relates to those weeds which are damaged only insufficiently or are not affected at all by the triazinones or triazinediones of the formulae (I), (II) or (III) which are used, when these are applied alone in customary amounts, the synergistic active compound combination according to the invention represents a valuable enrichment of the prior art.

Formulae (I), (II) and (III) given definitions of the triazinones or triazinediones to be used for the active compound combination according to the invention.

Of these, the triazinones of the formulae (I) and (II) are preferred. The triazinone of the formula (I) is particularly preferred.

The compounds of the formulae (I), (II) and (III) are known (see DE-OS (German Published Specification) No. 1,542,757, DE-OS (German Published Specification) No. 2,107,757 and DE-OS (German Published Specification) No. 2,254,200).

Formula (IV) gives a general definition of the halogenocarboxylic acid amides furthermore to be used as components of the mixture.

Among these, preferred halogenocarboxylic acid amides of the formula (IV) are those in which
R represents halogenoalkyl having up to 6 carbon atoms and up to 5 identical or different halogen atoms, in particular fluorine, chlorine or bromine, and $R^1$ and $R^2$ are identical or different and represent alkyl which has up to 8 carbon atoms and is optionally substituted by—halogen, cyano, nitro, hydroxyl, mercapto, alkoxy, cycloalkyl, halogenocycloalkyl, alkylcarbonyl, alkoxycarbonyl, alkylcarbonyloxy, alkylthiocarbonyloxy, alkoxycarbonyloxy, halogenoalkylcarbonyl, halogenoalkylcarbonyloxy, alkylcarbamyloxy, alkenylcarbamyloxy, cycloalkylcarbamyloxy, halogenophenylcarbamyloxy, halogenoalkylamido, halogenoalkyl-N-alkylamido, alkylsulphonyloxy, alkoximinoalkyl, phenyl which is optionally substituted by halogen, nitro, alkyl, dioxyalkylene, halogenophenoxyalkylamidoalkyl or halogenoalkylacetamido, heteroaryl which is optionally substituted by halogen, cyano or alkyl, piperidinyl, tetrahydrofuranyl, amino, N-alkylamino or N,N-dialkylamino, or N-(halogenoalkyl-carbonyl)-amino or N-(halogenoalkylamidoalkyl)-amino which is optionally substituted at the nitrogen atom by alkyl, alkanoyl or halogenoalkanoyl—or represent alkenyl which has up to 8 carbon atoms and is optionally substituted by—halogen, cyano, alkoxy, halogenoalkoxy, alkylcarbonyl, halogenoalkylcarbonyl, alkoxycarbonyl, amino, N-alkylamino, N,N-dialkylamino or halogenoalkylamido—or represent alkinyl having up to 6 carbon atoms, cycloalkyl which has 3 to 7 carbon atoms and is optionally substituted by lower alkyl, or represent cycloalkenyl having 3 to 7 carbon atoms, amino, alkylthio or alkylideneamino, each having up to 6 carbon atoms, formyl, alkylcarbonyl or alkoxycarbonyl, each having up to 6 carbon atoms, halogenoalkylcarbonyl, halogenoalkoxycarbonyl, halogenoalkylamido or halogenoalkyl-N-alkylamido, each having up to 6 carbon atoms in the alkyl parts and up to 5 halogen atoms, in particular fluorine, chlorine and bromine, and phenylsulphonyl or phenyl which is optionally substituted by—halogen, hydroxyl, alkyl, halogenoalkyl, alkoxy, alkylcarbonyl, halogenoalkylcarbonyl, alkylcarbonylalkenyl, alkylcarbamyloxy, alkenylcarbamyloxy, alkylamido, halogenoalkylamido or phthalimido— or heteroaryl which has 5 to 7 ring members and 1 to 3 hetero aroms, in particular nitrogen, oxygen and/or sulphur, and is optionally substituted by halogen, cyano, alkyl or polyalkylene or is benzo-fused, or $R^1$ and $R^2$, together with the nitrogen atom to which they are bonded, represent piperidinyl or piperidonyl which is optionally substituted by—alkyl, cycloalkyl-alkyl, alkoxy, dioxyalkylene, cyano, halogen, hydroxyl, alkylcarbonyl, halogenoalkylcarbonyl-piperidinylalkyl, piperidinyl or phenyl— or represent perhydroazepinyl, perhydroazocinyl, optionally halogenophenyl-substituted dihydropyrazolyl, perhydro-1,3-oxazinyl or morholinyl which is optionally substituted by lower alkyl, or perhydro-1,4-diazepinyl or 1,4-piperazinyl which is optionally substituted by—alkyl, phenylalkyl, phenylalkenyl, formyl, alkylcarbonyl, alkoxycarbonyl, halogenoalkylcarbonyl, or pyridyl, naphthyl or phenyl which is substituted by alkyl, alkoxy, halogen, halogenoalkyl, alkylcarbonyl or nitro— or represent dihydro- or perhydroindolyl, dihydro- or tetrahydropyridyl or dihydro-, tetrahydro- or perhydroquinolyl or -isoquinolyl which is optionally substituted by lower alkyl, azabicyclononyl, or oxazolidinyl or pyrrolidinyl which is optionally substituted by lower alkyl.

Particularly preferred compounds of the formula (IV) are those
in which
R represents halogenoalkyl having 1 to 3 carbon atoms and 1 to 5 halogen atoms, in particular chlorine, and $R^1$ and $R^2$ are identical or different and represent hydrogen, straight-chain or branched alkyl alkenyl or alkinyl, each having up to 4 carbon atoms, alkoxyalkyl, dialkoxyalkyl, alkoxyalkenyl, aminoalkyl, N-alkylaminoalkyl or N,N-dialkylaminoalkyl, each having up to 6 carbon atoms, cycloalkyl which has 3 to 7 carbon atoms and is optionally monosubstituted to trisubstituted by methyl and/or ethyl, cycloalkylalkyl which has 3 to 7 carbon atoms in the cycloalkyl part and 1 to 3 carbon atoms in the alkyl part and is optionally monosubstituted to trisubstituted by fluorine, chlorine and/or bromine, straight-chain or branched halogenoalkoxyalkenyl having up to 6 carbon atoms and up to 5 halogen atoms, in particular fluorine, chlorine and/or bromine, dihalogenoacetamidoalkyl or dihalogenoacetamidoalkylaminoalkyl, each of which has up to 4 carbon atoms in the alkyl parts and fluorine, chlorine and/or bromine as halogen and is optionally substituted at the nitrogen by methyl, ethyl, acetyl or dihalogenoacetyl, methoxy- or ethoxycarbonylalkyl and methoxy or ethoxycarbonylalkenyl having up to 4 carbon atoms in the alkyl or alkenyl part, acetyl- or dihalogenoacetylalkyl or -alkenyl having up to 4 carbon atoms in the alkyl or alkenyl part and fluorine, chlorine and/or bromine as halogen, methoximino- or ethoximinoalkyl having up to 4 carbon atoms in the alkyl part, phenylsulphonyl or phenyl which is optionally monosubstituted to trisubstituted by identical or different substituents from amongst alkyl having up to 4 carbon atoms, fluorine, chlorine, bromine, trifluoromethyl, trichloromethyl, acetyl and dichloroacetyl, mono-, di- or trihalogenoacetyl or propionyl having fluorine, chlorine and/or bromine as halogen atoms, heteroarylalkyl which has up to 4 carbon atoms in the alkyl part and 5 to 7 ring members in the heteroaryl part wherein 1 to 3 hetero atoms, in particular nitrogen, oxygen and/or sulphur can occur, and is optionally monosubstituted to trisubstituted by identical or different substituents from amongst alkyl having up to 4 carbon atoms, fluorine, chlorine, bromine and/or cyano, heteroaryl which has 5 to 7 ring members and 1 to 3 hetero atoms, in particular nitrogen, oxygen and/or sulphur, and is optionally monosubstituted or trisubstituted by identical or different substituents from amongst alkyl having up to 4 carbon atoms, fluorine, chlorine, bromine and/or cyano, or represent dibenzofuranyl or benzo-[e]-1,3-dioxanyl, or $R^1$ and $R^2$, together with the nitrogen atom to which they are bonded, represent piperid-4-on-1-yl or piperidin-1-yl which is optionally monosubstituted to pentasubstituted by identical or different substituents from amongst alkyl and alkoxy, each having up to 4 carbon atoms, cycloalkylalkyl having 3 to 7 carbon atoms in the cycloalkyl part and 1 to 3 carbon atoms in the alkyl part, hydroxyl, cyano, fluorine, chlorine, bromine, phenyl, piperidinyl, acetyl, dichloroacetyl, dioxyethylene or -propylene and/or dichloroacetylpiperidylalkyl having up to 4 carbon atoms in the alkyl part, or represent perhydroazepinyl or perhydroazocinyl, or 4,5-dihydropyrazolyl which has fluorine, chlorine and/or bromine as halogen atoms and is optionally substituted by mono- to penta-halogenophenyl, perhydro-1,3-oxazinyl or morpholinyl which is optionally monosubstituted or trisubstituted by identical or different alkyl radicals having up to 4 carbon atoms, or represent 1,4-piperazinyl or perhydro-1,4-diazepinyl which is optionally monosubstituted or trisubstituted by —alkyl having up to 4 carbon atoms, phenylalkyl or phenylalkenyl having up to 4 carbon atoms in the alkyl or alkenyl part, naphthyl, pyridyl, formyl, dichloroacetyl, chloropropionyl, methoxycarbonyl, ethoxycarbonyl or phenyl which is optionally monosubstituted to trisubstituted by identical or different substituents—particularly suitable phenyl substituents being: methyl, ethyl, methoxy, ethoxy, fluorine, chlorine, bromine, nitro, trifluoromethyl, acetyl and/or dichloroacetyl, and represent dihydro- or perhydroindolyl or dihydro-, tetrahydro- or perhydroquinolyl or -isoquinolyl which is optionally monosubstituted to pentasubstituted by identical or different substituents from amongst methyl and/or ethyl.

Very particularly preferred compounds of the formula (IV) are those
in which
R represents dichloromethyl and 1-chloro-ethyl, and
$R^1$ and $R^2$ are identical or different and represent hydrogen, methyl, ethyl, n- and i-propyl, allyl, prop-2-enyl, allenyl or propargyl, or represent propyl, propenyl, butyl, butenyl or ethyl which is monosubstituted to trisubstituted by methoxy, ethoxy, methoxycarbonyl, ethoxycarbonyl, acetyl, methoximino, ethoximino, dimethylamino, fluorine, chlorine and/or bromine, or represent dichloroacetyl, dichloroacetamidoethyl or -propyl, N-methyl-dichloroacetamidoethyl or -propyl, (N,N'-dimethyldichloroacetamidoethylaminoethyl or -propyl or (N-dichloroacetyl-N-dichloroacetamidopropyl)-amino-ethyl or -propyl, or represent cyclohexyl which is monosubstituted to trisubstituted by methyl and/or ethyl, cyclohexylmethyl or cyclopropylmethyl which is monosubstituted to trisubstituted by chlorine, or thiazolylmethyl or -ethyl, pyrazolylmethyl or -ethyl, oxadiazolylmethyl or -ethyl, oxathiazolylmethyl or -ethyl, pyridylmethyl or -ethyl, pyrimidylmethyl or -ethyl, thiadiazolylmethyl or -ethyl or oxazolylmethyl or -ethyl which is monosubstituted to trisubstituted by methyl, ethyl, propyl or butyl, phenyl which is monosubstituted to trisubstituted by identical or different substituents from amongst methyl, ethyl, propyl, butyl, chlorine, fluorine, bromine, trifluoromethyl, acetyl and/or dichloroacetyl, or represent dibenzofuranyl or benzo-[e]-1,3-dioxanyl, or represent thiadiazolyl which is substituted by methyl or ethyl, or $R^1$ and $R^2$, together with the nitrogen atom to which they are bonded, represent piperid-4-on-1-yl or piperidin-1-yl which is optionally monosubstituted to pentasubstituted by identical or different substituents from amongst methyl, ethyl, propyl, cyclohexylmethyl, hydroxyl, cyano, fluorine, chlorine, bromine, acetyl, dichloroacetyl, methoxy, ethoxy, dioxyethylene, dioxypropylene, phenyl, dichloroacetylpiperidylethyl or dichloroacetylpiperidylpropyl, 4,5-dihydropyrazolyl which is optionally substituted by 4-chlorophenyl, perhydro-1,3-oxazinyl or morpholinyl which is optionally monosubstituted to trisubstituted by methyl, or perhydro-1,4-diazepinyl or 1,4-piperazinyl which is optionally monosubstituted to trisubstituted by identical or different substituents from amongst methyl, ethyl, propyl, dichloroacetyl, chloropropionyl, methoxycarbonyl, ethoxycarbonyl, naphthyl, pyridyl, benzyl, phenylethyl, phenylpropyl, phenylpropenyl and phenyl which is optionally monosubstituted to trisubstituted by identical or different substituents, very particularly preferred phenyl substituents being: methyl, ethyl, methoxy, ethoxy, fluorine, chlorine, bromine, nitro, trifluoromethyl, acetyl and dichloroacetyl, and represent dihydro or perhydroquinolyl or dihydro-, tetrahydro- or perhydroquinolyl or -isoquinolyl which is optionally monosubstituted to pentasubstituted by methyl.

The following may be mentioned as individual examples of compounds of the formula (IV):

TABLE 1

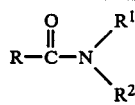

| R | $R^1$ | $R^2$ | $-N\begin{smallmatrix}R^1\\R^2\end{smallmatrix}$ | Example No. |
|---|---|---|---|---|
| $Cl_2CH-$ | | | 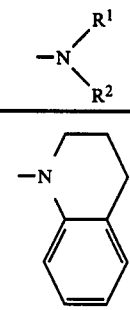 | 1 |

TABLE 1-continued
$$R-\overset{O}{\underset{}{C}}-N\overset{R^1}{\underset{R^2}{}} \quad (IV)$$
| R | R¹ | R² | $-N\overset{R^1}{\underset{R^2}{}}$ | Example No. |
|---|---|---|---|---|
| Cl₂CH— | | | 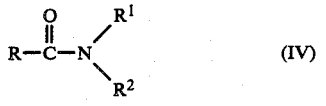 | 2 |
| Cl₂CH— | | | 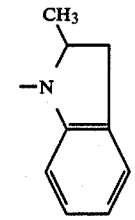 | 3 |
| Cl₂CH— | | | 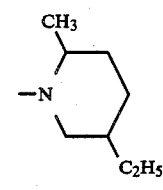 | 4 |
| Cl₂CH— | | | 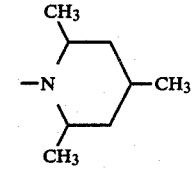 | 5 |
| Cl₂CH— | | | 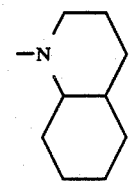 | 6 |
| Cl₂CH— | | | 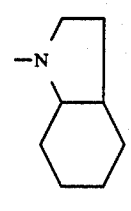 | 7 |

TABLE 1-continued $$R-\overset{\overset{O}{\|}}{C}-N\overset{R^1}{\underset{R^2}{}} \quad (IV)$$

| R | R¹ | R² | $-N\overset{R^1}{\underset{R^2}{}}$ | Example No. |
|---|---|---|---|---|
| Cl₂CH— | | | 2-methyl-1,2,3,4-tetrahydroisoquinolin-2-yl | 8 |
| Cl₂CH | | | 2-methyl-1,2,3,4-tetrahydroquinolin-1-yl | 9 |
| Cl₂CH— | | | 4-methyl-decahydroquinolin-1-yl | 10 |
| Cl₂CH— | | | 6-methyl-decahydroquinolin-1-yl | 11 |
| Cl₂CH— | | | 2,4-dimethylpiperidin-1-yl | 12 |
| Cl₂CH— | | | 2-methyl-decahydroquinolin-1-yl | 13 |

TABLE 1-continued
$$R-\overset{\overset{O}{\|}}{C}-N\overset{R^1}{\underset{R^2}{\diagdown}} \quad (IV)$$
| R | R¹ | R² | $-N\overset{R^1}{\underset{R^2}{\diagdown}}$ | Example No. |
|---|----|----|----|---|
| Cl₂CH— | | | 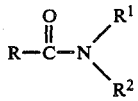 | 14 |
| Cl₂CH— | | | 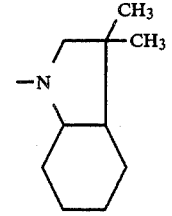 | 15 |
| Cl₂CH— | | | 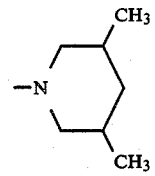 | 16 |
| Cl₂CH— | | | 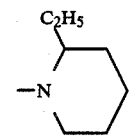 | 17 |
| Cl₂CH— | | | 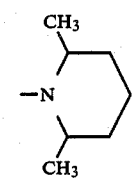 | 18 |
| Cl₂CH— | | | 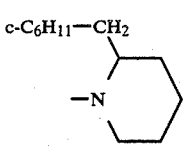 | 19 |
| Cl₂CH— | | | 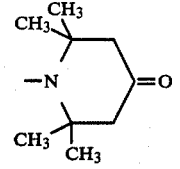 | 20 |

TABLE 1-continued $$R-\overset{O}{\underset{}{C}}-N\overset{R^1}{\underset{R^2}{}} \quad (IV)$$

| R | R¹ | R² | $-N\overset{R^1}{\underset{R^2}{}}$ | Example No. |
|---|---|---|---|---|
| Cl₂CH— | | | 2,2,4-trimethyl-1,2,3,4-tetrahydroquinolin-1-yl | 21 |
| Cl₂CH— | | | 4-phenylpiperazin-1-yl | 22 |
| Cl₂CH— | | | 4-benzylpiperazin-1-yl | 23 |
| Cl₂CH— | | | 1,4-dioxa-8-azaspiro[4.5]decan-8-yl | 24 |
| Cl₂CH— | | | 4-(4-methoxyphenyl)piperazin-1-yl | 25 |
| Cl₂CH— | | | 4-[3-(trifluoromethyl)phenyl]piperazin-1-yl | 26 |
| Cl—CH(CH₃)— | | | 1,2,3,4-tetrahydroisoquinolin-2-yl | 27 |
| Cl—CH(CH₃)— | | | 2-methyl-1,2,3,4-tetrahydroquinolin-1-yl | 28 |
| Cl₂CH— | | | 1,5-dioxa-9-azaspiro[5.5]undecan-9-yl | 29 |

TABLE 1-continued
$$R-\overset{\overset{O}{\|}}{C}-\underset{R^2}{\overset{R^1}{N}} \quad (IV)$$
| R | R¹ | R² | −N(R¹)(R²) | Example No. |
|---|---|---|---|---|
| Cl₂CH— | | | 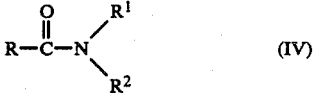 | 30 |
| Cl₂CH— | | | 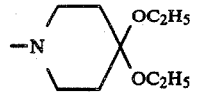 | 31 |
| Cl—CH(CH₃)— | | | 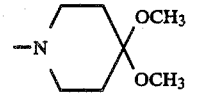 | 32 |
| Cl—CH(CH₃)— | | |  | 33 |
| Cl—CH(CH₃)— | | | 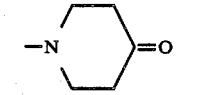 | 34 |
| Cl—CH(CH₃)— | | |  | 35 |
| Cl₂CH— | H |  | | 36 |
| Cl₂CH— | H |  | | 37 |
| Cl₂CH— | C₂H₅ | 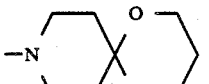 | | 38 |
| Cl₂CH— | C₂H₅ |  | | 39 |
| Cl—CH(CH₃)— | | | 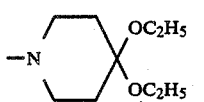 | 40 |

TABLE 1-continued
$$R-\overset{O}{\underset{}{C}}-N\overset{R^1}{\underset{R^2}{}} \quad (IV)$$
| R | R¹ | R² | $-N\overset{R^1}{\underset{R^2}{}}$ | Example No. |
|---|---|---|---|---|
| Cl—CH(CH₃)— | | | 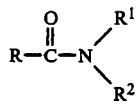 | 41 |
| Cl₂CH— | CH₃ |  | | 42 |
| Cl₂CH— | H |  | | 43 |
| Cl₂CH— | | |  | 44 |
| Cl₂CH— | | | 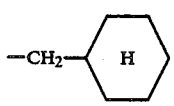 | 45 |
| Cl₂CH— | | |  | 46 |
| Cl₂CH— | | | 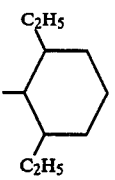 | 47 |
| Cl—CH(CH₃)— | | |  | 48 |
| Cl₂CH— | | | 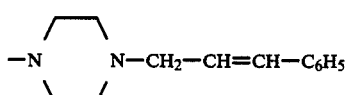 | 49 |
| Cl₂CH— | | |  | 50 |

TABLE 1-continued $$R-\underset{\underset{O}{\|}}{C}-N\underset{R^2}{\overset{R^1}{<}} \quad (IV)$$

| R | R¹ | R² | $-N\overset{R^1}{\underset{R^2}{<}}$ | Example No. |
|---|---|---|---|---|
| Cl₂CH— | | | —N(piperazine)N—CH₂—CH₂—C₆H₅ | 51 |
| Cl₂CH— | | | —N(piperazine)N—(2,6-dimethylphenyl) | 52 |
| Cl₂CH— | | | —N(piperazine)N—CH(CH₃)—C₆H₅ | 53 |
| Cl₂CH— | | | —N(piperazine)N—COOC₂H₅ | 54 |
| Cl₂CH— | | | —N(piperazine)N—(2-nitrophenyl) | 55 |
| Cl₂CH— | | | —N(piperazine)N—(4-nitrophenyl) | 56 |
| Cl₂CH— | | | —N(piperazine)N—(3-methylphenyl) | 57 |
| Cl₂CH— | | | —N(piperazine)N—(3-methoxyphenyl) | 58 |
| Cl₂CH— | | | —N(piperazine)N—(2-chlorophenyl) | 59 |
| Cl₂CH— | | | —N(piperazine)N—(2-fluorophenyl) | 60 |

TABLE 1-continued
$$R-\overset{O}{\underset{}{C}}-N\overset{R^1}{\underset{R^2}{}} \quad (IV)$$
| R | R¹ | R² | $-N\overset{R^1}{\underset{R^2}{}}$ | Example No. |
|---|---|---|---|---|
| Cl—CH(CH₃)— | | |  | 61 |
| Cl—CH(CH₃)— | | | 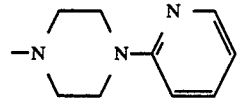 | 62 |
| Cl—CH(CH₃)— | | |  | 63 |
| Cl—CH(CH₃)— | | | 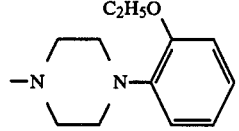 | 64 |
| Cl—CH(CH₃)— | | | 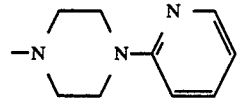 | 65 |
| Cl—CH(CH₃)— | | | —N(piperazine)N—COOC₂H₅ | 66 |
| Cl₂CH— | | | 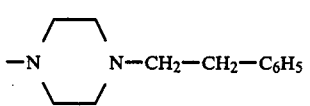 | 67 |
| Cl₂CH— | | |  | 68 |
| Cl₂CH— | | | 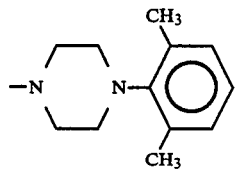 | 69 |
| Cl—CH(CH₃)— | | |  | 70 |

TABLE 1-continued $$R-\overset{\overset{O}{\|}}{C}-N\overset{R^1}{\underset{R^2}{\diagdown}} \quad (IV)$$

| R | R¹ | R² | $-N\overset{R^1}{\underset{R^2}{\diagdown}}$ | Example No. |
|---|---|---|---|---|
| Cl₂CH— | | | —N(piperazine)—C₆H₄—CH₃ (4-methylphenyl) | 71 |
| CH₃-CHCl— | | | —N(piperazine)N—CH₃ | 72 |
| Cl₂CH— | | | —N(homopiperazine)N—C(=O)—CHCl₂ | 73 |
| CH₃-CHCl— | | | —N(homopiperazine)N—C(=O)—CH(CH₃)—Cl | 74 |
| Cl₂CH— | | | —N(piperazine)N—CH₃ | 75 |
| CH₃-CHCl— | | | —N(piperazine)N—CH₃ | 76 |
| Cl₂CH— | | | —N(piperazine)—C₆H₄—C(=O)CH₃ | 77 |
| Cl₂CH— | | | —N(piperazine)N—C(=O)—H | 78 |
| Cl₂CH— | | | —N(piperazine)N—CH₂—CH₂—CH₃ | 79 |
| Cl₂CH— | | | —N(4-oxopiperidine) | 80 |
| Cl₂CH— | | | —N(piperidine)-(piperidinyl) | 81 |

TABLE 1-continued $$R-\overset{O}{\underset{\|}{C}}-N\overset{R^1}{\underset{R^2}{\diagdown}} \quad (IV)$$

| R | R¹ | R² | $-N\diagup^{R^1}_{\diagdown R^2}$ | Example No. |
|---|---|---|---|---|
| Cl₂CH— | | | 4-cyano-4-phenylpiperidin-1-yl | 82 |
| Cl₂CH— | | | 1-methylhexahydroazepin-1-yl (N-methyl azepane) | 83 |
| Cl₂CH— | | | 4-methylpiperazin-1-yl (homopiperazine, N'-CH₃) | 84 |
| Cl₂CH— | | | —N(piperidin-4-yl)(CH₂)₃(piperidin-4-yl)N—C(O)—CHCl₂ | 85 |
| Cl₂CH— | | | 4-bromo-4-phenylpiperidin-1-yl | 86 |
| Cl₂CH— | | | 3-(4-chlorophenyl)-4,5-dihydropyrazol-1-yl | 87 |
| Cl₂CH— | | | 4-(dichloroacetyl)piperazin-1-yl | 88 |
| CH₃-CHCl— | | | 4-(2-chloropropanoyl)piperazin-1-yl | 89 |
| Cl₂CH— | | | 4-acetyl-4-phenylpiperidin-1-yl | 90 |
| Cl₂CH— | CH₃ | —(CH₂)₂—N(CH₃)—(CH₂)₂—N(CH₃)—C(O)—CHCl₂ | | 91 |

TABLE 1-continued $$R-\overset{O}{\underset{}{C}}-N\overset{R^1}{\underset{R^2}{}} \quad (IV)$$

| R | R¹ | R² | $-N\overset{R^1}{\underset{R^2}{}}$ | Example No. |
|---|---|---|---|---|
| Cl₂CH— | (4-methylphenyl)-C(=O)-CH₃ | —C(=O)—CHCl₂ | | 92 |
| CH₃-CHCl— | | | N-methylpiperazinyl with 3-(trifluoromethyl)phenyl | 93 |
| Cl₂CH— | | | 2,6-dimethylpiperazine-N-C(=O)-CHCl₂ | 94 |
| Cl₂CH— | | | 2,6-dimethylpiperazine-N-C(=O)-CHCl₂ | 95 |
| CH₃-CHCl— | | | 2,6-dimethylpiperazine-N-C(=O)-CH(CH₃)Cl | 96 |
| CH₃-CHCl— | | | 2,6-dimethylpiperazine-N-C(=O)-CH(CH₃)Cl | 97 |
| Cl₂CH— | | | 3-methylpiperazine-N-C(=O)-CHCl₂ | 98 |
| Cl₂CH— | | | 3,3,6-trimethylmorpholine | 99 |

TABLE 1-continued $$R-\overset{\overset{O}{\|}}{C}-N\overset{R^1}{\underset{R^2}{<}} \quad (IV)$$

| R | R¹ | R² | $-N\overset{R^1}{\underset{R^2}{<}}$ | Example No. |
|---|---|---|---|---|
| Cl₂CH— | | | 1,2-dihydro-2,2,4-trimethylquinolin-1-yl | 100 |
| Cl₂CH— | | | 1,2-dihydro-2,2,4,8-tetramethylquinolin-1-yl | 101 |
| Cl₂CH— | H | —(CH₂)₂—NH—C(=O)—CHCl₂ | | 102 |
| Cl₂CH— | H | —(CH₂)₃—N(CH₃)—C(=O)—CHCl₂ | | 103 |
| Cl₂CH— | H | —(CH₂)₃—N[C(=O)CHCl₂]—(CH₂)₃—NH—C(=O)—CHCl₂ | | 104 |
| Cl₂CH— | H | —CH₂—CH₂—N(CH₃)₂ | | 105 |
| Cl₂CH— | | | 4-(4-methoxyphenyl)-3-methylpiperazin-1-yl | 106 |
| Cl₂CH— | | | hexahydroazepin-1-yl | 107 |
| Cl₂CH— | —CH₂—CH=CH₂ | —CH₂—CH=N—OCH₃ | | 108 |
| Cl₂CH— | —CH₂—C≡CH | —CH₂—CH(OCH₃)₂ | | 109 |
| Cl₂CH— | —CH₃ | —CH₂—C≡CH | | 110 |

TABLE 1-continued $$R-\overset{O}{\underset{}{C}}-N\overset{R^1}{\underset{R^2}{}} \quad (IV)$$

| R | R¹ | R² | $-N\overset{R^1}{\underset{R^2}{}}$ | Example No. |
|---|---|---|---|---|
| Cl₂CH— | —CH₃ | —CH=C=CH₂ | | 111 |
| CH₃-CHCl- (Cl—CH(CH₃)—) | —CH₂—CH=CH₂ | —CH₂—C(=O)—CH₃ | | 112 |
| Cl₂CH— | —CH₂—CH=CH₂ | —CH₂—(isoxazole) | | 113 |
| Cl₂CH— | —CH₂—CH=CH₂ | —CH₂—(thiazole-CH₃) | | 114 |
| Cl—CH(CH₃)— | —CH₂—CH=CH₂ | —CH₂—C(CH₃)=N—OCH₃ | | 115 |
| Cl—CH(CH₃)— | —CH₂—CH=CH₂ | —CH₂—C(=N—O—)C(CH₃)=N | | 116 |
| Cl₂CH— | —CH₂—CH=CH₂ | —CH₂—(CCl₂ cyclopropyl) | | 117 |
| Cl₂CH— | —CH₂—CH=CH₂ | —CH₂—(isoxazole) | | 118 |
| Cl—CH(CH₃)— | —CH₂—CH=CH₂ | —CH₂—CH=N—OCH₃ | | 119 |
| Cl₂CH— | CH₃ | 2,6-diethylphenyl | | 120 |
| Cl₂CH— | 2,6-diethylphenyl | —CH₂—N(pyrazole) | | 121 |
| Cl₂CH— | H | 2,6-diethylphenyl | | 122 |

TABLE 1-continued $$R-\overset{O}{\underset{}{C}}-N\overset{R^1}{\underset{R^2}{}} \quad (IV)$$

| R | R¹ | R² | $-N\overset{R^1}{\underset{R^2}{}}$ | Example No. |
|---|---|---|---|---|
| Cl₂CH— | 2-CH₃, 6-C₂H₅-phenyl | —CH₂—N(pyrazolyl) | | 123 |
| Cl₂CH— | H | 2-CH₃, 6-C₂H₅-phenyl | | 124 |
| Cl₂CH— | H | 2-(CH₃)₃C-phenyl | | 125 |
| Cl₂CH— | H | 2,6-(CH₃)₂-phenyl | | 126 |
| Cl₂CH— | H | 3,5-(CH₃)₂-phenyl | | 127 |
| Cl₂CH— | CH₃ | 2,6-(CH₃)₂-phenyl | | 128 |
| Cl₂CH— | 2,6-(C₂H₅)₂-phenyl | —CH(CH₂—OCH₃)—C(Cl)=CH₂ | | 129 |
| Cl₂CH— | —CH₂—CH₂—CH₃ | —CH₂—CH₂—CH₃ | | 130 |
| Cl₂CH— | | | —N(morpholino) | 131 |

TABLE 1-continued $$R-\overset{\overset{O}{\|}}{C}-\overset{R^1}{\underset{R^2}{N}} \quad (IV)$$

| R | R¹ | R² | $-N\overset{R^1}{\underset{R^2}{}}$ | Example No. |
|---|---|---|---|---|
| Cl₂CH— | | | | 132 |
| Cl₂CH— | CH₃ | CH(CH₃)₂-phenyl | | 133 |
| Cl₂CH— | —C₂H₅ | C₂H₅-phenyl | | 134 |
| Cl₂CH— | CH₃ | C₂H₅-phenyl | | 135 |
| Cl₂CH— | —CH₂—CH=CH₂ | —CH₂—CH₂—N(pyrazole) | | 136 |
| Cl₂CH— | —CH₂—CH=CH₂ | —CH₂-(pyrimidine) | | 137 |
| Cl₂CH— | —CH₂—CH=CH₂ | —CH₂-(4,6-dimethylpyrimidine) | | 138 |
| CH₃-CHCl— | —CH₂—CH=CH₂ | —CH₂-(4,6-dimethylpyrimidine) | | 139 |
| CH₃-CHCl— | —CH₂—CH=CH₂ | —CH₂-(pyrimidine) | | 140 |
| Cl₂CH— | —CH₂—CH=CH₂ | (3,5-dimethylisothiazole) | | 141 |

TABLE 1-continued $$R-\overset{O}{\underset{}{C}}-N\overset{R^1}{\underset{R^2}{}}\quad(IV)$$

| R | R¹ | R² | $-N\overset{R^1}{\underset{R^2}{}}$ | Example No. |
|---|---|---|---|---|
| CH₃-CHCl- | -CH₂-CH=CH₂ | 3-methyl-5-methyl-1,2,4-thiadiazol-yl | | 142 |
| Cl₂CH- | -CH₂-C(CH₃)=CH₂ | 2,6-dimethylphenyl | | 143 |
| Cl₂CH- | -CH₂-CH=CH₂ | 3-ethyl-isoxazol-5-yl-methyl | | 144 |
| Cl₂CH- | -CH₂-CH=CH₂ | 4-methyl-isoxazol-3-yl-methyl | | 145 |
| Cl₂CH- | -CH₂-CH=CH₂ | 4-methyl-isoxazol-3-yl-(1-methylethyl) | | 146 |
| Cl₂CH- | -CH₂-CH=CH₂ | 4-propyl-isoxazol-3-yl-methyl | | 147 |
| CH₃-CHCl- | 2,6-dimethylphenyl | -CH(CH₃)-COOCH₃ | | 148 |
| Cl₂CH- | 2,6-dimethylphenyl | -CH(CH₃)-COOCH₃ | | 149 |
| Cl₂CH- | 2-methyl-6-ethylphenyl | -CH(CH₃)-COOC₂H₅ | | 150 |

TABLE 1-continued $$R-\overset{O}{\overset{\|}{C}}-N\overset{R^1}{\underset{R^2}{\diagdown}} \quad (IV)$$

| R | R¹ | R² | $-N\diagdown_{R^2}^{R^1}$ | Example No. |
|---|---|---|---|---|
| Cl₂CH— | 2,6-diethylphenyl | —CH(CH₃)—COOC₂H₅ | | 151 |
| Cl₂CH— | 2,6-diethylphenyl (CH₃ top, C₂H₅ bottom) | —CH(CH₃)—COOCH₃ | | 152 |
| Cl₂CH— | CH₃ | CH₃ | | 153 |
| Cl₂CH— | C₂H₅ | —C₂H₅ | | 154 |
| CH₃CHCl— | | | piperidino | 155 |
| CH₃CHCl— | | | 2,6-dimethylpiperidino | 156 |
| CH₃CHCl— | | | 3,5-dimethylpiperidino | 157 |
| CH₃CHCl— | —CH₂—CH=CH₂ | —CH₂—CH=CH₂ | | 158 |
| Cl₂CH— | 2,6-dimethylphenyl | —C(CH₃)=CH—COCH₃ | | 159 |
| Cl₂CH— | 2,6-dimethylphenyl | —C(CH₃)=CH—COOC₂H₅ | | 160 |

TABLE 1-continued $$\underset{R^2}{\overset{R^1}{\underset{|}{R-C-N}}}\overset{O}{\overset{\|}{}} \quad (IV)$$

| R | R¹ | R² | $-N\begin{smallmatrix}R^1\\R^2\end{smallmatrix}$ | Example No. |
|---|---|---|---|---|
| Cl₂CH— | 3,5-bis(CF₃)-phenyl | $\underset{|}{\overset{CH_3}{-C}}=CH-COCH_3$ | | 161 |
| Cl₂CH— | 2-CH₃, 4-C₂H₅-phenyl | $\underset{|}{\overset{CH_3}{-C}}=CH-COCH_3$ | | 162 |
| Cl₂CH— | 2-CH₃, 4-Cl-phenyl | $\underset{|}{\overset{CH_3}{-C}}=CH-COCH_3$ | | 163 |
| Cl₂CH— | 3-CF₃-phenyl | $\underset{|}{\overset{CH_3}{-C}}=CH-COCH_3$ | | 164 |

Some of the compounds of the formula (IV) are known (see, for example, DE-OS (German Published Specification) No. 2,218,097, DE-OS (German Published Specification) No. 2,828,293, DE-OS (German Published Specification) No. 2,828,222, DE-OS (German Published Specification) No. 2,828,331, DE-OS (German Published Specification) No. 2,828,265 DE-OS (German Published Specification) No. 2,930,448, DE-OS (German Published Specification) No. 2,930,449, DE-OS (German published Specification) No. 2,913,459, DE-OS (German Published Specification) No. 2,930,450, DE-OS (German Published Specification) No. 2,930,451, DE-OS (German Published Specification) No. 2,930,452, DE-OS (German Published Specification) No. 2,938,155, DE-OS (German Published Specification) No. 3,004,871 and DE-OS (German Published Specification) No. 3,035,356).

Compounds of this type which are hitherto unknown can be prepared in an analogous, simple manner by known processes. They are obtained, for example, by reacting corresponding halogenocarboxylic acid chlorides with appropriate amines, if appropriate in the presence of a diluent, such as, for example, dichloromethane, and if appropriate in the presence of an acid-binding agent, such as, for example, triethylamine, at temperatures between −80° C. and +100° C., preferably between −10° C. and +40° C.

The weight ratios of the active compound groups can vary within relatively wide ranges. In general, 0.25 to 100, preferably 5 to 50, in particular 10 to 20, parts by weight of halogenocarboxylic acid amide of the formula (IV) (synergistic agent) are employed per part by weight of the triazinone or triazinedione of the formulae (I), (II) or (III) (herbicidal active compound).

The herbicides from the group comprising the triazinones or triazinediones of the formulae (I), (II) or (III) possess powerful herbicidal actions. Nevertheless, their action against some weeds, such as, for example, *Galium aparine, Ipomea hederacea, Datura stramonium, Cirsium arrense, Convolvulus arvarsis* or *Solanum nigrum,* and some graminaceous weeds, such as, for example, *Agropyron repens, Avena fatua, Cynodon dactylon,* Cyperus ssp. and *Colium rigidum,* is not always adequate. The active compound combination according to the invention extends the action spectrum of triazinone and triazinedione herbicides, and hence also makes it possible to combat these weeds which can be combated only with difficulty, if at all, by the herbicidal triazinones or triazinediones.

The active compound combinations according to the invention can be used, for example, in connection with the following plants:

Dicotyledon weeds of the genera:

Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera:

Gossypium, Glycine, Beta, Daucus, Phaseolus, Pisum, Solanum, Linum, Ipomoea, Vicia, Nicotiana, Lycopersicon, Arachis, Brassica, Lactuca; Cucumis and Cucurbita.

Monocotyledon weeds of the genera:

Aechinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera:

Oryza, Zea, Triticum, Hordeum, Avena, Secale, Sorghum, Panicum, Saccharum, Ananas, Asparagus and Allium.

However, the use of the active compound combinations according to the invention is in no way restricted to these genera, but also extends in the same manner to other plants.

In addition to a good action against graminaceous weeds, the active compound combinations according to the invention also exhibit, in particular, a good herbicidal action in broad-leaved weeds. In addition, the active compound combinations according to the invention also possess a good action against fungal pathogens in plants, such as, for example, against the causative organisms of rice diseases, *Pyricularia oryzae* and *Pellicularia sasakii*, and also against fungal pathogens from the class of the Oomycetes.

The active compound combinations according to the invention can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is, liquid solvents and/or solid carriers, optionally with the use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives, such as carboxymethylcellulose and natural and synthetic polymers in the form of powders, granules or latices, such as gum arabic, polyvinyl alcohol and polyvinyl acetate, can be used in the formulations.

In the formulations it is possible to use, as further additives, colorants such as inorganic pigments, for example iron oxide, titanium oxide and Prussian Blue, and organic dyestuffs, such as alizarin dyestuffs and azo-metal phthalocyanine dyestuffs, and trace nutrients such as salts of iron, manganese, boron, copper, cobalt, molybdenum and zinc.

The formulations in general contain between 0.1 and 95 percent by weight of active compound combination, preferably between 0.5 and 90%.

The active compound combinations according to the invention are used in general in the form of finished formulations. However, the active compounds present in the active compound combinations can also be mixed as individual formulations when being used, that is to say they can be used in the form of tank mixtures.

The new active compound combinations, as such or in the form of their formulations, can furthermore also be used as mixtures with other known herbicides, finished formulations or tank mixtures once again being possible. Mixtures with other known active compounds, such as fungicides, insecticides, acaricides, nematicides, bird repellents, growth factors, plant nutrients and agents which improve soil structure, are also possible.

The new active compound combinations can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, dusting or scattering.

The active compound combinations according to the invention can be applied, together with or separately from other substances, either before or after sowing or after emergence of the plants. The sequence in which the substances are applied is not critical.

When the synergistic agents according to the invention are employed, the customary use amounts of the particular herbicides can be reduced. In treating an area, the amount of herbicidal triazinone or triazinedione component used is between 0.01 and 3.0 kg/ha, preferably between 0.05 and 2.0 kg/ha. In treating an area, the amount of synergistic halogenocarboxylic acid amide used is between 0.1 and 10 kg/ha, preferably between 0.5 and 3 kg/ha.

The good herbicidal action of the active compound combinations according to the invention can be seen from the example which follows. While the individual active compounds have weaknesses in herbicidal action, the combination shows a very broad action against weeds, which goes beyond a simple additive action.

A synergistic effect exists with herbicides whenever the herbicidal action of the active compound combination is greater than the sum of the actions of the individually applied active compounds.

EXAMPLE A

Pre-emergence Test

Solvent: 5 parts by weight of acetone
Emulsifier: 1 part by weight of alkylaryl polyglycol ether To produce a suitable preparation of active compound, 1 part by weight of active compound or synergistic agent or a mixture of herbicidal active compound and synergistic agent is mixed with the stated amount of solvent, the stated amount of emulsifier is added and the concentrate is diluted with water to the desired concentration.

Seeds of the test plants are sown in normal soil and, after 24 hours, watered with a herbicide preparation or with the preparation of the synergistic agent or with the preparation of the synergistic agent and herbicidally active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

Active compounds, amount applied and results can be seen from Tables A and B which follow.

TABLE A

Pre-emergence test
Synergistic effect of halogenocarboxylic acid amides (IV) (= synergistic agent S) and
4-amino-6-t-butyl-3-methylthio-1,2,4-triazin-5-one (I) (= herbicide H) in *Ipomoea hederifolia*.
The amount applied in kg/ha is relative to the content of active compound.

$$R-\overset{O}{\underset{\|}{C}}-N\overset{R^1}{\underset{R^2}{\diagdown}}$$

| Example No. | (IV) | (S) kg/ha | (H) kg/ha | H | S | H + S |
|---|---|---|---|---|---|---|
| (144) | CH$_2$=CH—CH$_2$—N(CO—CHCl$_2$)—CH$_2$-[oxadiazole]-C$_2$H$_5$ | 0.5 | 0.05 | 0 | 0 | 0 |
|  |  | 2 | 0.05 | 0 | 0 | 0 |
|  |  | 0.5 | 0.15 | 0 | 0 | 0 |
|  |  | 2 | 0.15 | 0 | 0 | 20 |
| (145) | CH$_2$=CH—CH$_2$—N(CO—CHCl$_2$)(CH$_2$-[oxadiazole]-CH$_3$) | 0.5 | 0.05 | 0 | 0 | 0 |
|  |  | 2 | 0.05 | 0 | 0 | 0 |
|  |  | 0.5 | 0.15 | 0 | 0 | 0 |
|  |  | 2 | 0.15 | 0 | 0 | 10 |
| (147) | CH$_2$=CH—CH$_2$—N(CO—CHCl$_2$)—CH$_2$-[oxadiazole]-CH$_2$—CH$_2$—CH$_3$ | 0.5 | 0.05 | 0 | 0 | 0 |
|  |  | 2 | 0.05 | 0 | 0 | 10 |
|  |  | 0.5 | 0.15 | 0 | 0 | 20 |
|  |  | 2 | 0.15 | 0 | 0 | 50 |
| (13) | [decahydroquinoline, N-CO-CHCl$_2$, 2-CH$_3$] | 0.5 | 0.05 | 0 | 0 | 0 |
|  |  | 2 | 0.05 | 0 | 0 | 0 |
|  |  | 0.5 | 0.15 | 0 | 0 | 0 |
|  |  | 2 | 0.15 | 0 | 0 | 100 |
| (15) | [3,5-dimethylpiperidine, N-CO-CHCl$_2$] | 0.5 | 0.05 | 0 | 0 | 0 |
|  |  | 2 | 0.05 | 0 | 0 | 20 |
|  |  | 0.5 | 0.15 | 20 | 0 | 60 |
|  |  | 2 | 0.15 | 20 | 0 | 80 |
| (16) | [2-ethylpiperidine, N-CO-CHCl$_2$] | 0.5 | 0.05 | 0 | 0 | 10 |
|  |  | 2 | 0.05 | 0 | 0 | 40 |
|  |  | 0.5 | 0.15 | 20 | 0 | 50 |
|  |  | 2 | 0.15 | 20 | 0 | 80 |

TABLE A-continued

Pre-emergence test
Synergistic effect of halogenocarboxylic acid amides (IV) (= synergistic agent S) and
4-amino-6-t-butyl-3-methylthio-1,2,4-triazin-5-one (I) (= herbicide H) in *Ipomoea hederifolia*.
The amount applied in kg/ha is relative to the content of active compound.

$$R-\overset{\overset{O}{\|}}{C}-N\overset{R^1}{\underset{R^2}{}}$$

| Example No. | (IV) | (S) kg/ha | (H) kg/ha | % damage H | S | H + S |
|---|---|---|---|---|---|---|
| (17) | 2,6-dimethylpiperidine-N-CO-CHCl₂ | 0.5 | 0.05 | 0 | 0 | 10 |
| | | 2 | 0.05 | 0 | 0 | 10 |
| | | 0.5 | 0.15 | 20 | 0 | 100 |
| | | 2 | 0.15 | 20 | 0 | 100 |
| (22) | phenyl-N-piperazine-N-CO-CHCl₂ | 0.5 | 0.05 | 0 | 0 | 0 |
| | | 2 | 0.05 | 0 | 0 | 0 |
| | | 0.5 | 0.15 | 20 | 0 | 30 |
| | | 2 | 0.15 | 20 | 0 | 60 |
| (28) | 2-methyl-1,2,3,4-tetrahydroquinoline-N-CO-CHCl-CH₃ | 0.5 | 0.05 | 0 | 0 | 0 |
| | | 2 | 0.05 | 0 | 0 | 20 |
| | | 0.5 | 0.15 | 10 | 0 | 20 |
| | | 2 | 0.15 | 10 | 0 | 30 |
| (83) | heptamethyleneimine-N-CO-CHCl₂ | 0.5 | 0.05 | 0 | 0 | 40 |
| | | 2 | 0.05 | 0 | 0 | 100 |
| | | 0.5 | 0.15 | 20 | 0 | 80 |
| | | 2 | 0.15 | 20 | 0 | 100 |
| (108) | Cl₂CH—CO—N(CH₂—CH=CH₂)(CH₂—CH=N—OCH₃) | 0.5 | 0.05 | 0 | 0 | 20 |
| | | 2 | 0.05 | 0 | 0 | 40 |
| | | 0.5 | 0.15 | 20 | 0 | 100 |
| | | 2 | 0.15 | 20 | 0 | 90 |
| (109) | Cl₂CH—CO—N(CH₂—C≡CH)(CH₂—CH(OCH₃)₂) | 0.5 | 0.05 | 0 | 0 | 20 |
| | | 2 | 0.05 | 0 | 0 | 70 |
| | | 0.5 | 0.15 | 20 | 0 | 90 |
| | | 2 | 0.15 | 20 | 0 | 100 |
| (110) | Cl₂CH—CO—N(CH₃)(CH₂—C≡CH) | 0.5 | 0.05 | 0 | 0 | 20 |
| | | 2 | 0.05 | 0 | 0 | 70 |
| | | 0.5 | 0.15 | 20 | 0 | 90 |
| | | 2 | 0.15 | 20 | 0 | 100 |
| (111) | Cl₂CH—CO—N(CH₃)(CH=C=CH₂) | 0.5 | 0.05 | 0 | 0 | 10 |
| | | 2 | 0.05 | 0 | 0 | 10 |
| | | 0.5 | 0.15 | 20 | 0 | 90 |
| | | 2 | 0.15 | 20 | 0 | 100 |
| (112) | CH₃—CHCl—CO—N(CH₂—CH=CH₂)(CH₂—CO—CH₃) | 0.5 | 0.05 | 0 | 0 | 50 |
| | | 2 | 0.05 | 0 | 0 | 100 |
| | | 0.5 | 0.15 | 20 | 0 | 80 |
| | | 2 | 0.15 | 20 | 0 | 70 |
| (113) | Cl₂CH—CO—N(CH₂-isoxazolyl)(CH₂—CH=CH₂) | 0.5 | 0.05 | 0 | 0 | 20 |
| | | 2 | 0.05 | 0 | 0 | 50 |
| | | 0.5 | 0.15 | 20 | 0 | 60 |
| | | 2 | 0.15 | 20 | 0 | 100 |

TABLE A-continued

Pre-emergence test
Synergistic effect of halogenocarboxylic acid amides (IV) (= synergistic agent S) and
4-amino-6-t-butyl-3-methylthio-1,2,4-triazin-5-one (I) (= herbicide H) in *Ipomoea hederifolia*.
The amount applied in kg/ha is relative to the content of active compound.

$$R-\underset{\underset{O}{\|}}{C}-N\underset{R^2}{\overset{R^1}{\diagdown}}$$

| Example No. | (IV) | (S) kg/ha | (H) kg/ha | % damage H | S | H + S |
|---|---|---|---|---|---|---|
| (114) | Cl$_2$CH—CO—N(CH$_2$-[thiazole-CH$_3$])(CH$_2$—CH=CH$_2$) | 0.5 | 0.05 | 0 | 0 | 10 |
| | | 2 | 0.05 | 0 | 0 | 20 |
| | | 0.5 | 0.15 | 20 | 0 | 40 |
| | | 2 | 0.15 | 20 | 0 | 50 |
| (115) | CH$_3$—CHCl—CO—N(CH$_2$—C(CH$_3$)=N—O—CH$_3$)(CH$_2$—CH=CH$_2$) | 0.5 | 0.05 | 0 | 0 | 10 |
| | | 2 | 0.05 | 0 | 0 | 40 |
| | | 0.5 | 0.15 | 20 | 0 | 60 |
| | | 2 | 0.15 | 20 | 0 | 100 |
| (117) | Cl$_2$CH—CO—N(CH$_2$—[cyclopropyl-Cl$_2$])(CH$_2$—CH=CH$_2$) | 0.5 | 0.05 | 0 | 0 | 0 |
| | | 2 | 0.05 | 0 | 0 | 20 |
| | | 0.5 | 0.15 | 0 | 0 | 10 |
| | | 2 | 0.15 | 0 | 0 | 80 |
| (119) | CH$_3$—CHCl—CO—N(CH$_3$—CH=N—OCH$_3$)(CH$_2$—CH=CH$_2$) | 0.5 | 0.05 | 0 | 0 | 50 |
| | | 2 | 0.05 | 0 | 0 | 90 |
| | | 0.5 | 0.15 | 0 | 0 | 70 |
| | | 2 | 0.15 | 0 | 0 | 90 |
| (136) | CH$_2$=CH—CH$_2$—N(CO—CHCl$_2$)(CH$_2$—CH$_2$—N[pyrazole]) | 0.5 | 0.05 | 0 | 0 | 40 |
| | | 2 | 0.05 | 0 | 0 | 40 |
| | | 0.5 | 0.15 | 0 | 0 | 80 |
| | | 2 | 0.15 | 0 | 0 | 100 |
| (158) | CH$_3$—CHCl—CO—N(CH$_2$—CH=CH$_2$)$_2$ | 0.5 | 0.05 | 0 | 0 | 80 |
| | | 2 | 0.05 | 0 | 0 | 90 |
| | | 0.5 | 0.15 | 20 | 0 | 100 |
| | | 2 | 0.15 | 20 | 0 | 100 |
| (153) | Cl$_2$CH—CO—N(CH$_3$)$_2$ | 0.5 | 0.05 | 0 | 0 | 0 |
| | | 2 | 0.05 | 0 | 0 | 10 |
| | | 0.5 | 0.15 | 20 | 0 | 10 |
| | | 2 | 0.15 | 20 | 0 | 40 |
| (154) | Cl$_2$CH—CO—N(C$_2$H$_5$)$_2$ | 0.5 | 0.05 | 0 | 0 | 30 |
| | | 2 | 0.05 | 0 | 0 | 100 |
| | | 0.5 | 0.15 | 20 | 0 | 90 |
| | | 2 | 0.15 | 20 | 0 | 90 |
| (155) | CH$_3$—CHCl—CO—N(piperidine) | 0.5 | 0.05 | 0 | 0 | 10 |
| | | 2 | 0.05 | 0 | 0 | 40 |
| | | 0.5 | 0.15 | 10 | 0 | 50 |
| | | 2 | 0.15 | 10 | 0 | 90 |
| (156) | CH$_3$—CHCl—CO—N(2,6-dimethylpiperidine) | 0.5 | 0.05 | 0 | 0 | 20 |
| | | 2 | 0.05 | 0 | 0 | 60 |
| | | 0.5 | 0.15 | 10 | 10 | 30 |
| | | 2 | 0.15 | 10 | 0 | 100 |

TABLE A-continued

Pre-emergence test
Synergistic effect of halogenocarboxylic acid amides (IV) (= synergistic agent S) and
4-amino-6-t-butyl-3-methylthio-1,2,4-triazin-5-one (I) (= herbicide H) in *Ipomoea hederifolia*.
The amount applied in kg/ha is relative to the content of active compound.

$$R-\overset{\overset{O}{\|}}{C}-N\overset{R^1}{\underset{R^2}{}}$$

| Example No. | (IV) | (S) kg/ha | (H) kg/ha | % damage H | S | H + S |
|---|---|---|---|---|---|---|
| (157) | CH₃—CH(Cl)—CO—N(2,5-dimethylpiperidine) | 0.5 | 0.05 | 0 | 0 | 40 |
|  |  | 2 | 0.05 | 0 | 0 | 80 |
|  |  | 0.5 | 0.15 | 10 | 0 | 80 |
|  |  | 2 | 0.15 | 10 | 0 | 100 |
| (2) | 2-methylindoline-N—CO—CHCl₂ | 0.5 | 0.05 | 0 | 0 | 10 |
|  |  | 2 | 0.05 | 0 | 0 | 10 |
|  |  | 0.5 | 0.15 | 0 | 0 | 0 |
|  |  | 2 | 0.15 | 0 | 0 | 20 |
| (5) | decahydroquinoline-N—CO—CHCl₂ | 0.5 | 0.05 | 0 | 0 | 0 |
|  |  | 2 | 0.05 | 0 | 0 | 0 |
|  |  | 0.5 | 0.15 | 0 | 0 | 20 |
|  |  | 2 | 0.15 | 0 | 0 | 10 |
| (6) | 2-methyloctahydroindole-N—CO—CHCl₂ | 0.5 | 0.05 | 0 | 0 | 0 |
|  |  | 2 | 0.05 | 0 | 0 | 0 |
|  |  | 0.5 | 0.15 | 0 | 0 | 0 |
|  |  | 2 | 0.15 | 0 | 0 | 20 |
| (23) | PhCH₂—N(piperazine)N—CO—CHCl₂ | 0.5 | 0.05 | 0 | 0 | 0 |
|  |  | 2 | 0.05 | 0 | 0 | 0 |
|  |  | 0.5 | 0.15 | 20 | 0 | 20 |
|  |  | 2 | 0.15 | 20 | 0 | 40 |
| (49) | 2-pyridyl-N(piperazine)N—CO—CHCl₂ | 0.5 | 0.05 | 0 | 0 | 0 |
|  |  | 2 | 0.05 | 0 | 0 | 0 |
|  |  | 0.5 | 0.15 | 10 | 0 | 0 |
|  |  | 2 | 0.15 | 10 | 0 | 30 |
| (95) | Cl₂CH—CO—N(2,5-dimethylpiperazine)N—CO—CHCl₂ (cis) | 0.5 | 0.05 | 0 | 0 | 0 |
|  |  | 2 | 0.05 | 0 | 0 | 0 |
|  |  | 0.5 | 0.15 | 10 | 0 | 10 |
|  |  | 2 | 0.15 | 10 | 0 | 30 |
| (124) | 2-methyl-6-ethylphenyl-NH—CO—CHCl₂ | 0.5 | 0.05 | 0 | 0 | 0 |
|  |  | 2 | 0.05 | 0 | 0 | 40 |
|  |  | 0.5 | 0.15 | 0 | 0 | 0 |
|  |  | 2 | 0.15 | 0 | 0 | 50 |

TABLE A-continued

Pre-emergence test
Synergistic effect of halogenocarboxylic acid amides (IV) (= synergistic agent S) and
4-amino-6-t-butyl-3-methylthio-1,2,4-triazin-5-one (I) (= herbicide H) in *Ipomoea hederifolia*.
The amount applied in kg/ha is relative to the content of active compound.

$$R-\overset{O}{\underset{\|}{C}}-N\overset{R^1}{\underset{R^2}{\diagdown}}$$

| Example No. | (IV) | (S) kg/ha | (H) kg/ha | % damage H | S | H + S |
|---|---|---|---|---|---|---|
| (128) | 2,6-dimethyl-N-methyl-N-(dichloroacetyl)aniline | 0.5 | 0.05 | 0 | 0 | 0 |
|  |  | 2 | 0.05 | 0 | 0 | 0 |
|  |  | 0.5 | 0.15 | 0 | 0 | 0 |
|  |  | 2 | 0.15 | 0 | 0 | 50 |
| (130) | Cl$_2$CH—CO—N(CH$_2$—CH$_2$—CH$_3$)$_2$ | 0.5 | 0.05 | 0 | 0 | 10 |
|  |  | 2 | 0.05 | 0 | 0 | 100 |
|  |  | 0.5 | 0.15 | 0 | 0 | 10 |
|  |  | 2 | 0.15 | 0 | 0 | 40 |
| (131) | morpholine-N—CO—CHCl$_2$ | 0.5 | 0.05 | 0 | 0 | 0 |
|  |  | 2 | 0.05 | 0 | 0 | 10 |
|  |  | 0.5 | 0.15 | 0 | 0 | 0 |
|  |  | 2 | 0.15 | 0 | 0 | 60 |
| (132) | piperidine-N—CO—CHCl$_2$ | 0.5 | 0.05 | 0 | 0 | 0 |
|  |  | 2 | 0.05 | 0 | 0 | 30 |
|  |  | 0.5 | 0.15 | 0 | 0 | 60 |
|  |  | 2 | 0.15 | 0 | 0 | 60 |
| (133) | 2-isopropyl-N-methyl-N-(dichloroacetyl)aniline | 0.5 | 0.05 | 0 | 0 | 0 |
|  |  | 2 | 0.05 | 0 | 0 | 0 |
|  |  | 0.5 | 0.15 | 0 | 0 | 10 |
|  |  | 2 | 0.15 | 0 | 0 | 20 |
| (134) | 2-ethyl-N-ethyl-N-(dichloroacetyl)aniline | 0.5 | 0.05 | 0 | 0 | 0 |
|  |  | 2 | 0.05 | 0 | 0 | 0 |
|  |  | 0.5 | 0.15 | 0 | 0 | 20 |
|  |  | 2 | 0.15 | 0 | 0 | 40 |
| (135) | 2-ethyl-N-methyl-N-(dichloroacetyl)aniline | 0.5 | 0.05 | 0 | 0 | 0 |
|  |  | 2 | 0.05 | 0 | 0 | 20 |
|  |  | 0.5 | 0.15 | 10 | 0 | 20 |
|  |  | 2 | 0.15 | 10 | 0 | 80 |
| (142) | CH$_3$—CHCl—CO—N(CH$_2$—CH=CH$_2$)(4-methyl-thiazol-2-yl) | 0.5 | 0.05 | 0 | 0 | 20 |
|  |  | 2 | 0.05 | 0 | 0 | 30 |
|  |  | 0.5 | 0.15 | 20 | 0 | 0 |
|  |  | 2 | 0.15 | 20 | 0 | 30 |
| (107) | Cl$_2$CH—CO—N(hexamethyleneimine) | 0.5 | 0.05 | 0 | 0 | 90 |
|  |  | 2 | 0.05 | 0 | 0 | 90 |
|  |  | 0.5 | 0.15 | 0 | 0 | 90 |
|  |  | 2 | 0.15 | 0 | 0 | 100 |

TABLE B

Pre-emergence test
Synergistic effect of dichloroacetylperhydroazocinide
(IV, Example 83) (= synergistic agent S) and the herbicidal
triazinones or triazinediones (I), (II) and (III) (= herbicide H)
in *Ipomoea heferifolia*. The amount applied in kg/ha is relative
to the content of active compound.

| Herbicide | (S) kg/ha | (H) kg/ha | % damage H | % damage S | % damage H + S |
|---|---|---|---|---|---|
| (I) (CH₃)₃C—C(=O)—C(=N—N=C(SCH₃))—N(NH₂) | 1 | 0.05 | 0 | 0 | 60 |
|  | 2 | 0.05 | 0 | 0 | 100 |
|  | 1 | 0.15 | 20 | 0 | 80 |
|  | 2 | 0.15 | 20 | 0 | 100 |
| (II) C₆H₅—C(=O)—C(=N—N=C(CH₃))—N(NH₂) | 1 | 1 | 0 | 0 | 0 |
|  | 2 | 1 | 0 | 0 | 0 |
|  | 1 | 4 | 0 | 0 | 20 |
|  | 2 | 4 | 0 | 0 | 30 |
| (III) (CH₃)₃C—CH₂—N—C(=O)—N(NH₂)—C(=N—N=C(SC₂H₅))—C(=O) | 1 | 0.5 | 50 | 0 | 80 |
|  | 2 | 0.5 | 50 | 0 | 90 |
|  | 1 | 2 | 90 | 0 | 90 |
|  | 2 | 2 | 90 | 0 | 100 |

Preparation Examples

Example 107

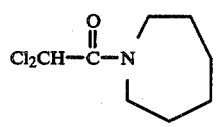

14.7 g (0.1 mol) of dichloroacetyl chloride are added dropwise to a solution of 10 g (0.1 mol) of hexamethyleneimine and 10 g (0.1 mol) of triethylamine in 200 ml of toluene at 20° C. During this procedure, the reaction temperature increases to 40°–50° C.

The mixture is stirred for a further 5 hours at 20°–25° C. The reaction mixture is then washed with 100 ml of water, with 100 ml of 10% strength hydrochloric acid and once again with 100 ml of water, and is then evaporated down. 18 g (85% of theory) of N-dichloroacetyl-perhydroazepine are obtained in the form of colorless crystals of melting point 56° C.

Example 83

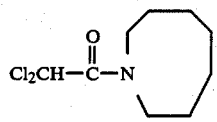

12.9 g (0.088 mol) of dichloroacetyl chloride are added dropwise to a mixture of 10 g (0.088 mol) of heptamethyleneimine, 9 g (0.09 mol) of triethylamine and 150 ml of toluene at 25° C.

The mixture is stirred for a further 12 hours at 20° C., and the reaction mixture is then washed with 100 ml of water, 100 ml of 10% strength hydrochloric acid and once again with 150 ml of water.

The solvent is then stripped off. 19 g (85% of theory) of N-dichloroacetyl-perhydroazocine are obtained in the form of colorless crystals of melting point 83° C.

The following compounds of the general formula (IV) are obtained in an analogous manner or on the basis of processes known from the literature:

TABLE 2

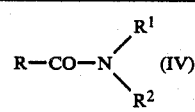

| Example No. | | Melting point (°C.) or refractive index $n_D^{20}$ |
|---|---|---|
| (109) | 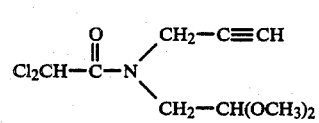 | 1.4936 |
| (110) | 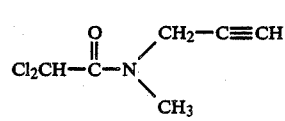 | 1.5118 |
| (111) | 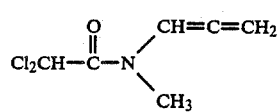 | 1.5400 |

TABLE 2-continued

| Example No. | Structure | Melting point (°C.) or refractive index $n_D^{20}$ |
|---|---|---|
| (112) | Cl—CH(CH$_3$)—C(O)—N(CH$_2$—CH=CH$_2$)(CH$_2$—C(O)—CH$_3$) | 1.4869 |
| (117) | Cl$_2$CH—C(O)—N(CH$_2$—CH=CH$_2$)(CH$_2$-cyclopropyl-Cl,Cl) | 1.5249 |
| (119) | Cl—CH(CH$_3$)—C(O)—N(CH$_2$—CH=CH$_2$)(CH$_2$—CH=N—OCH$_3$) | 1.4873 |
| (95) | Cl$_2$CH—C(O)—N[CH$_2$CH(CH$_3$)]$_2$N—C(O)—CHCl$_2$ (piperazine) | 225 |
| (124) | Cl$_2$CH—C(O)—NH—(2-CH$_3$, 6-C$_2$H$_5$-phenyl) | 151 |

Compounds of the general formula (IV)/

$$R-\overset{O}{\underset{\phantom{O}}{C}}-N\overset{R^1}{\underset{R^2}{\phantom{-}}} \quad (IV)$$

| Example No. | Structure | Melting point (°C.) or refractive index $n_D^{20}$ |
|---|---|---|
| (87) | Cl$_2$CH—C(O)—N—N=CH—(4-Cl-phenyl) (pyrazoline) | 152 |
| (159) | Cl$_2$CH—C(O)—N(2,6-(CH$_3$)$_2$-phenyl)(C(CH$_3$)=CH—CO—CH$_3$) | 84–86 |

TABLE 2-continued

| Example No. | Structure | Melting point (°C.) or refractive index $n_D^{20}$ |
|---|---|---|
| (160) | $Cl_2CH-\underset{\underset{O}{\|}}{C}-N(\text{2,6-(CH}_3)_2\text{C}_6\text{H}_3)-C(CH_3)=CH-COOC_2H_5$ | 85 |
| (162) | $Cl_2CH-\underset{\underset{O}{\|}}{C}-N(\text{2-CH}_3\text{-6-C}_2\text{H}_5\text{C}_6\text{H}_3)-C(CH_3)=CH-CO-CH_3$ | 72 |
| (163) | $Cl_2CH-\underset{\underset{O}{\|}}{C}-N(\text{2-CH}_3\text{-6-Cl-C}_6\text{H}_3)-C(CH_3)=CH-CO-CH_3$ | 106 |
| (128) | $Cl_2CH-\underset{\underset{O}{\|}}{C}-N(CH_3)(\text{2,6-(CH}_3)_2\text{C}_6\text{H}_3)$ | 98 |
| (133) | $Cl_2CH-\underset{\underset{O}{\|}}{C}-N(CH_3)(\text{2-CH(CH}_3)_2\text{C}_6\text{H}_4)$ | 64 |
| (134) | $Cl_2CH-\underset{\underset{O}{\|}}{C}-N(C_2H_5)(\text{2-C}_2\text{H}_5\text{C}_6\text{H}_4)$ | Oil |
| (135) | $Cl_2CH-\underset{\underset{O}{\|}}{C}-N(CH_3)(\text{2-C}_2\text{H}_5\text{C}_6\text{H}_4)$ | Oil |
| (148) | $CH_3-CHCl-\underset{\underset{O}{\|}}{C}-N(\text{2,6-(CH}_3)_2\text{C}_6\text{H}_3)-CH(CH_3)-COOCH_3$ | 105.5–106 |

TABLE 2-continued

| Example No. | | Melting point (°C.) or refractive index $n_D^{20}$ |
|---|---|---|
| (84) | Cl₂CH—C(=O)—N(piperazine)N—CH₃ | Oil |
| (85) | Cl₂CH—C(=O)—N(piperidine)—(CH₂)₃—(piperidine)N—C(=O)—CHCl₂ | 76 |
| (161) | Cl₂CH—C(=O)—N[C(CH₃)=CO—CH₃] on 3,5-bis(CF₃)phenyl | 123 |
| (164) | Cl₂CH—C(=O)—N[C(CH₃)=CH—COCH₃] on 3-CF₃-phenyl | Oil |
| (158) | CH₃—CHCl—C(=O)—N(CH₂—CH=CH₂)₂ | Oil |

It is understood that the specification and examples are illustrative but not limitative of the present invention and that other embodiments within the spirit and scope of the invention will suggest themselves to those skilled in the art.

What is claimed is:

1. A herbicidal composition comprising a selectively herbicidally effective amount of a combination of (A) a triazinone or triazinedione of the formula

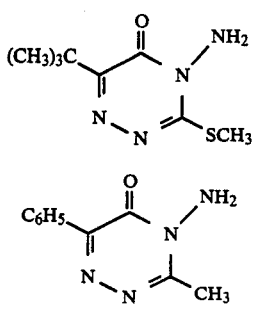

or

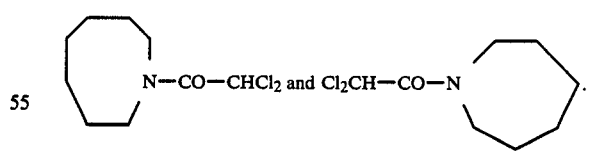

and (B) an excess up to about 50 times its weight of a synergistically effective amount of a halogenocarboxylic acid amide selected from the group consisting of N—CO—CHCl₂ and Cl₂CH—CO—N (with cycloheptyl groups).

2. A herbicidal composition according to claim 1, wherein the weight ratio of (A) triazinone or triazinedione herbicide to (B) halogenocarboxylic acid amide synergist is between about 1:5 and 1:50.

3. A herbicidal composition according to claim 1, wherein the weight ratio of (A) triazinone or triazinedione herbicide to (B) halogenocarboxylic acid amide synergist is between about 1:10 and 1:20.

4. A herbicidal composition according to claim 1, wherein the synergist (B) is

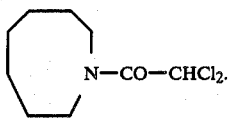

5. A herbicidal composition according to claim 1, wherein the synergist (B) is

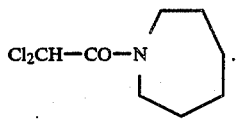

6. A herbicidal composition according to claim 1, where (A) is of the formula

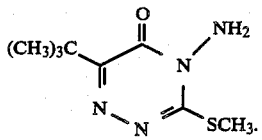

7. A method of combating unwanted vegetation which comprises applying to such vegetation or to a locus where such vegetation is to be grown a selectively herbicidally effective amount of a composition according to claim 1.

8. The method according to claim 7, wherein the synergist (B) is

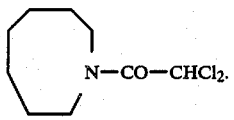

9. The method according to claim 7, wherein the synergist (B) is

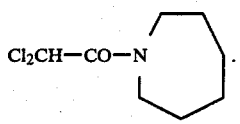

10. The method according to claim 7, wherein (A) is of the formula

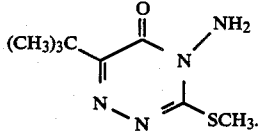

* * * * *